US005798366A

United States Patent [19]
Platt et al.

[11] Patent Number: 5,798,366
[45] Date of Patent: Aug. 25, 1998

[54] METHOD FOR TREATMENT OF CNS-INVOLVED LYSOSOMAL STORAGE DISEASES

[75] Inventors: Frances M. Platt, Oxford, United Kingdom; Gabrielle R. Neises, Chesterfield, Mo.; Raymond A. Dwek; Terry D. Butters, both of Oxford, United Kingdom

[73] Assignee: Monsanto Company, St. Louis, Mo.

[21] Appl. No.: 782,321

[22] Filed: Jan. 13, 1997

Related U.S. Application Data

[63] Continuation-in-part of Ser. No. 393,640, Feb. 24, 1995, Pat. No. 5,656,641, and Ser. No. 588,027, Jan. 17, 1996, which is a division of Ser. No. 396,989, Mar. 1, 1995, Pat. No. 5,580,884, which is a division of Ser. No. 102,654, Aug. 5, 1993, which is a continuation-in-part of Ser. No. 61,645, May 13, 1993, Pat. No. 5,399,567, said Ser. No. 393,640, is a continuation of Ser. No. 61,645.

[51] Int. Cl.$^6$ .................................................. A61K 31/445
[52] U.S. Cl. .................................................................. 514/315
[58] Field of Search ........................................... 514/315

[56] References Cited

U.S. PATENT DOCUMENTS

| 4,065,562 | 12/1977 | Ohata et al. | 424/267 |
|---|---|---|---|
| 4,182,767 | 1/1980 | Murai et al. | 424/267 |
| 4,533,668 | 8/1985 | Matsumara et al. | 514/321 |
| 4,639,436 | 1/1987 | Junge et al. | 514/24 |
| 4,849,430 | 7/1989 | Fleet et al. | 514/315 |
| 5,011,829 | 4/1991 | Hirsch et al. | 514/50 |
| 5,030,638 | 7/1991 | Partis et al. | 514/315 |

OTHER PUBLICATIONS

Saunier et al., J. Biol. Chem. 257, 14155–14161 (1982).
Elbein, Ann. Rev. Biochem. 56, 497–534 (1987).
NewBrun, Arch. Oral Biol. 28, 531–536 (1982).
Wang et al., Tetrahedron Lett. 34, 403–406 (1993).
Karlsson et al., J. Biol. Chem. 268, 570–576 (1993).
Shukla et al., Biochem. Biophys. Acta 1083, 101–108 (1991).
Shukla and Radin, J. Lipid Res. 32, 713–722 (1991).
Basu, J. Biol. Chem. 248, 1388–1394 (1973).
van Heyningen, Nature 249, 415–417 (1974).
Karlsson, Ann. Rev. Biochem. 58, 309–350 (1989).
Platt et al., Eur. J. Biochem 208, 187–193 (1992).
Butters and Hughes, In Vitro 17, 831–838 (1981).
Platt et al., J. Biol. Chem. 269, 8362–8365 (1994).
Platt et al., J. Biol.Chem. 269, 27108–27114 (1994).
Yamanaka et al., Proc. Natl. Acad. Sci. 91, 9975–9979 (1994).

*Primary Examiner*—William R. A. Jarvis
*Attorney, Agent, or Firm*—Scott J. Meyer

[57] ABSTRACT

A method is disclosed for the in vivo treatment of patients having a lysosomal storage disease with a significant central nervous system (CNS) involvement. Said method comprises administration to said patient a small but storage-inhibitory effective amount of an N-alkyl derivative of a 1,5-iminosugar in which said alkyl group contains from about 2 to about 8 carbon atoms and said 1,5-iminosugar is 1,5-dideoxy-1,5-imino-D-glucitol, or 1,5-dideoxy-1,5-imino-D-galactitol, or an O-acylated pro-drug of said 1,5-iminosugar. In an illustrative example, CNS storage of GM2 ganglioside is inhibited in Tay-Sachs mice by administration of 1,5-(butylimino)-1,5-dideoxy-D-glucitol.

6 Claims, 6 Drawing Sheets

METHOD FOR TREATMENT OF CNS-INVOLVED LYSOSOMAL STORAGE DISEASES

CROSS-REFERENCE TO RELATED APPLICATIONS

This is a continuation-in-part of application Ser. No. 08/393,640, filed Feb. 24, 1995, now U.S. Pat. No. 5,656,641, which is a continuation of application Ser. No. 08/061,645, filed May 13, 1993, now U.S. Pat. No. 5,399,567, and this is a continuation-in-part of application Ser. No. 08/588,027, filed Jan. 17, 1996, which is a division of application Ser. No. 08/396,989, filed Mar. 1, 1995, now U.S. Pat. No. 5,580,884 which is a division of application Ser. No. 08/102,654, filed Aug. 5, 1993, which is a continuation-in-part of said application Ser. No. 08/061,645, filed May 13, 1993, now U.S. Pat. No. 5,399,567.

BACKGROUND AND FIELD OF THE INVENTION

This invention relates to a method for the treatment of lysosomal storage diseases that have a significant central nervous system (CNS) involvement. These diseases are caused by genetic mutations which result in the absence or deficiency of lysosomal enzymes. They include, for example, Tay-Sachs disease, Sandhoff disease, GM1 gangliosidosis and Fabry disease.

A list of references indicated by numerals in parentheses is appended at the end.

Tay-Sachs Disease

This is a fatal hereditary disorder of lipid metabolism characterized especially in CNS tissue due to deficiency of the A (acidic) isozyme of β-hexosaminidase. Mutations in the HEXA gene, which encodes the α subunit of β-hexosaminidase, cause the A isozyme deficiency. Tay-Sachs [disease] is a prototype of a group of disorders, the GM2 gangliosidoses, characterized by defective GM2 ganglioside degradation. The GM2 ganglioside (monosialylated ganglioside 2) accumulates in the neurons beginning already in fetal life.

Sandhoff Disease

Sandhoff disease results from a deficiency of both the A and B (basic) isozymes of β-hexosaminidase. Mutations in the HEXB gene, which encodes the β subunit of β-hexosaminidase, cause the B isozyme deficiency.

GM1 Gangliodidosis

GM1 gangliosidosis is caused by a deficiency of β-galactosidase, which results in lysosomal storage of GM1 ganglioside (monosialylated ganglioside 1).

Fabry Disease

Fabry disease is caused by a deficiency of α-galactosidase which results in lysosomal storage of a ceramide trihexoside.

Glycosphingolipid (GSL) storage diseases are a group of human autosomal recessive disorders (except Fabry disease which is X-linked), each of which exhibits a characteristic pathology (1). They result from the inheritance of defects in genes encoding the catabolic enzymes required for the complete breakdown of GSLs within the lysosomes.

There presently is no effective therapy for Tay-Sachs disease or other lysosomal storage diseases with CNS involvement. Proposed strategies for the treatment of these debilitating and often fatal diseases include enzyme replacement therapy, gene therapy, substrate deprivation, allogenic bone marrow transplantation and palliative measures (2). Of these, symptomatic management is the only approach for treating most of these disorders, although transplantation techniques have been applied to some of these diseases.

Currently, only the non-neuronopathic form of Gaucher disease (type 1), a condition characterized by glucocerebrosidase deficiency, which occurs at high frequency in Ashkenazi Jews, has been successfully treated using enzyme replacement therapy (3,4). However, skeletal abnormalities associated with the disease respond slowly to this treatment (4) and the rare type 2 (acute neuronopathic;infantile) and rare type 3 (chronic;juvenile) are refractory to therapy.

Accordingly, new therapeutic treatment for lysosomal storage diseases which have significant CNS involvement (neuronopathic) are urgently needed.

BRIEF DESCRIPTION OF THE INVENTION

In accordance with the present invention, a method is provided for the in vivo treatment of patients having a lysosomal storage disease with a significant CNS involvement.

Said method comprises administration to said patient of a small but storage-inhibitory effective amount of an N-alkyl derivative of a 1,5-iminosugar in which said alkyl group contains from about 2 to about 8 carbon atoms and said 1,5-iminosugar is 1,5-dideoxy-1,5-imino-D-glucitol, or 1,5-dideoxy-1,5-imino-Dgalactitol, or an O-acylated pro-drug of said 1,5-iminosugar.

Preferred 1,5-iminosugars are:

1,5-(Butylimino)-1,5-dideoxy-D-glucitol, which is also known as N-butyl deoxynojirimycin or by the abbreviated designation N-butyl DNJ;

1,5-(Butylimino)-1,5-dideoxy-D-galactitol, which is also known as N-butyl deoxygalactonojirimycin or by the abbreviated designation N-butyl DGJ;

1,5-(Butylimino)-1,5-dideoxy-D-glucitol, tetrabutyrate; and 1,5-(Butylimino)-1,5-dideoxy-D-galactitol, tetrabutyrate.

The method of the invention is illustrated in detail herein with the preferred compound, N-butyl DNJ. As described in detail herein, a mouse model of Tay-Sachs disease (9) is used to illustrate the in vivo effect of the 1,5-iminosugars for treatment of lysosomal storage diseases having a significant CNS involvement. Using this mouse model, it was demonstrated with the illustrative N-butyl DNJ that this agent unexpectedly was able to cross the blood:brain barrier to an extent which inhibited CNS storage of GM2 ganglioside compared to the untreated control mice which exhibit progressive storage of that ganglioside.

DETAILED DESCRIPTION OF THE INVENTION

While the specification concludes with claims particularly pointing out and distinctly claiming the subject matter regarded as forming the invention, it is believed that the invention will be better understood from the following illustrative detailed description taken in conjunction with the accompanying drawings.

BRIEF DESCRIPTION OF THE DRAWINGS

FIG. 2, in two parts, A and B, shows prevention of GM2 storage in 12 week old mice. To demonstrate the variation in GM2 storage in mice treated with NB-DNJ, a group of three untreated and three NB-DNJ treated mice were compared at 12 weeks of age.

FIG. 3, in four parts, A–D, shows GM2 storage in the ventromedial hypothalamus of untreated and NB-DNJ treated mice (12 weeks of age). Frozen sections were stained with periodic acid-Schiff (PAS) to allow the visualization of GM2 storing neurons.

The sections were selected to ensure that sections from the two animals were comparable in terms of spatial orientation within the brain. The images shown are representative of data derived from four different pairs of mice. The reduction in PAS staining in NB-DNJ treated mice was also observed in other storage regions of the brain.

FIG. 4, in four parts, A–D, shows electron microscopy of brains from untreated and NB-DNJ treated mice.

Figure 4A:
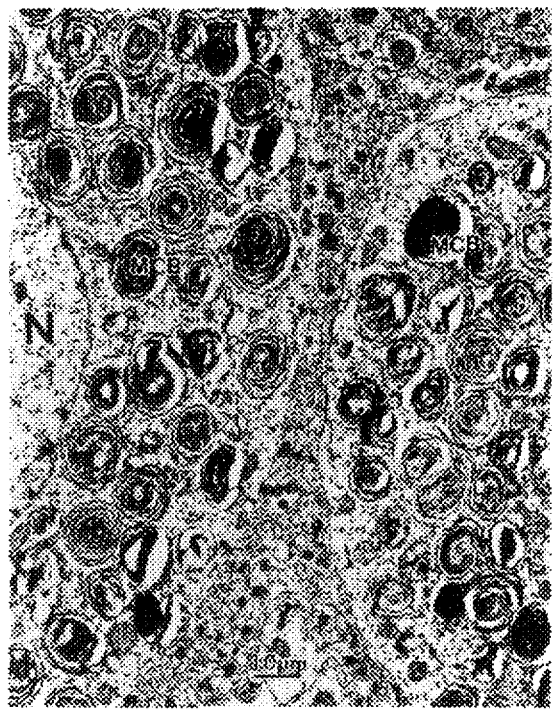
Figure 4B:
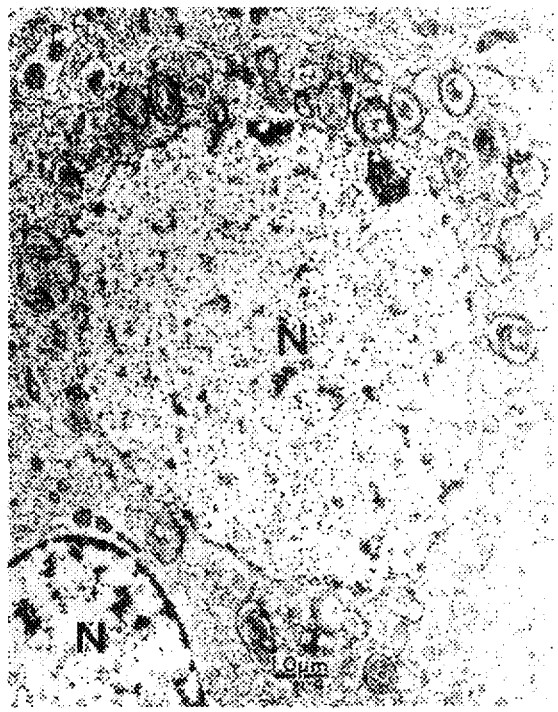
Figure 4C:
Figure 4D:
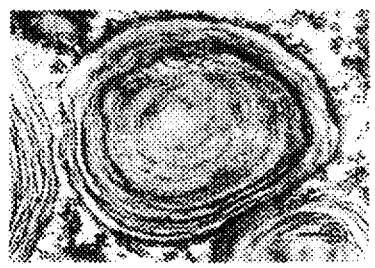

FIG. 4A: GM2 storage neuron from an untreated mouse brain;

FIG. 4B: GM2 storage neuron from an NB-DNJ treated mouse brain (the scale bar for A and B represents 1 µm;

FIG. 4C: MCBs (membranous cytoplasmic bodies) from an untreated mouse brain;

FIG. 4D: MCBs from an NB-DNJ treated mouse brain (the scale bar for C and D represents 0.1 µm).

The data shown are representative on the basis of analyzing multiple sections for multiple storage regions of the brain from two untreated and two NB-DNJ treated animals, with the analysis carried out by two independent groups.

Figure 5:
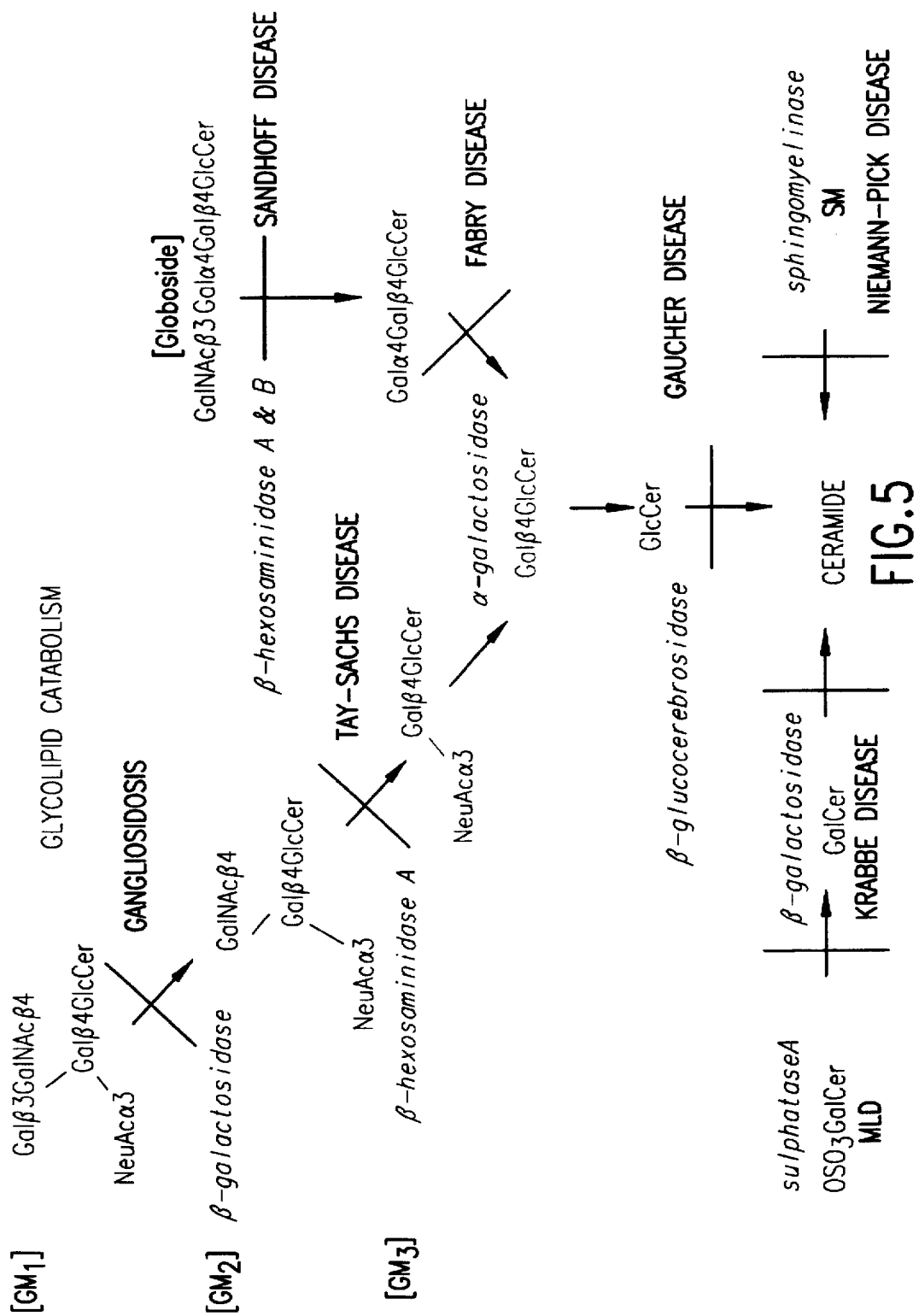

FIG. 5 is a schematic flow chart which shows glycolipid catabolism and the relationship of lysosomal storage diseases to the absence or deficiency of relevant enzyme to degrade a given ganglioside or globoside. Of the lysosomal storage diseases that have a significant CNS involvement:

GM1 gangliosidosis is shown to be caused by a deficiency in β-galactosidase;

Tay-Sachs disease, which is a GM2 gangliosidosis, is shown to be caused by a deficiency of β-hexosaminidase A (acidic isozyme);

Sandhoff disease is shown to be caused by a deficiency of βhexosaminidase A & B (acidic and basic isozymes); and Fabry disease is shown to be caused by a deficiency in α-galactosidase.

In a different step of the GlcCer pathway, Gaucher disease is shown to be caused by a deficiency in β-glucocerebrosidase. Three diseases shown at the bottom of FIG. 5, namely metachromatic leukodystrophy (MLD), Krabbe disease and Niemann-Pick disease, involve different metabolic pathways, the GalCer pathway and sphingomyelinase (SM) pathway.

The mouse model of Tay-Sachs disease (9) is a useful model for demonstrating the in vivo effectiveness of the 1,5-iminosugars for the treatment of lysosomal storage diseases having a significant CNS involvement since this model has all the hallmarks of Tay-Sachs disease.

Tay-Sachs disease results from mutations in the HEXA gene, which encodes the a subunit of β-hexosaminidase, leading to a deficiency in the A isoenzyme. The A isoenzyme is responsible for the degradation of GM2 ganglioside. When this enzyme is deficient in humans, GM2 ganglioside accumulates progressively and leads to severe neurological degeneration (10).

In the mouse model of Tay-Sachs disease (generated by the targeted disruption of the Hexa gene), the mice store GM2 ganglioside in a progressive fashion, but the levels never exceed the threshold required to elicit neurodegeneration (9).

This is because in the mouse (but not human) a sialidase is sufficiently abundant that it can convert GM2 to GA2 (asialo ganglioside 2), which can then be catabolized by the hexosaminidase B isoenzyme (11). This model therefore has all the hallmarks of Tay-Sachs disease, in that it stores GM2 ganglioside in the CNS, but it never develops the neurological symptoms characteristic of the human disease (9,11, 12).

In order to thus further illustrate the invention, the following detailed examples were carried out although it will be understood that the invention is not limited to these specific examples or the details described therein.

EXAMPLE I

Tay-Sachs mice were reared on standard mouse chow up to the age of weaning (4 weeks post-partum) when they were placed on a powdered mouse chow diet containing NB-DNJ as follows:

Mice were fed on a diet of powdered mouse chow (expanded Rat and Mouse Chow 1, ground, SDS Ltd., Witham, Essex, UK) containing NB-DNJ from weaning (4 weeks). The diet and compound (both dry solids) were mixed thoroughly before use, stored at room temperature and used within seven days of mixing. Water was available to the mice ad lib. The mice were housed under standard non-sterile conditions. The mice were given a dosing regime of 4800 mg/kg/day of NB-DNJ which gave serum levels of approximately 50 µM.

Similar serum levels (steady state trough level of approximately 20 µM) were achieved in humans during the evaluation of this compound as an anti-viral agent when patients were treated with 43 mg/kg/day (12).

The pharmacokinetics of NB-DNJ are two orders of magnitude poorer in mouse relative to human, thereby necessitating high dosing regimes in the mouse in order to achieve serum levels in the predicted therapeutic range for the GSL storage disorders of 5–50 µM (5–8).

EXAMPLE II

The effects that drug administration had on GM2 storage in the Tay-Sachs mouse were determined at various ages by extracting total brain lipids, separating the base resistant GSL fraction by TLC (FIG. 1), and identifying the GM2 species on the basis of comigration with an authentic GM2 standard. The following procedure was employed:

The animals were anesthetized, perfused with phosphate buffered saline, pH 7.2, and the intact brain removed. The brain tissue was manually homogenized in water, freeze-dried and extracted twice with chloroform:methanol 2:1 (v/v) for two hours at room temperature and overnight at 4° C.

A volume of the solvent extract equivalent to 5 mg dry weight for each brain was dried under nitrogen, taken up in 500 µl chloroform:methanol (1:1 v/v), 83 µl of 0.35 M NaOH in 96% methanol added and incubated at room temperature for 90 mins. The samples were partitioned by adding 83 µl $H_2O$:methanol (9:1 v/v), 166.5 µl $H_2O$ and 416 µl chloroform, spun in a microfuge for 1 min and the upper phase retained. The lower phase was washed twice in Folch theoretical upper phase (chloroform:methanol:water, 1:10:10 v/v/v) and the upper phases retained and pooled with the original upper phase.

The samples were partially dried under $N_2$ to remove the solvent and the residual aqueous sample made up to 1 ml with $H_2O$ and dialyzed overnight in 2 liters of water to desalt. The samples were freeze-dried, extracted with 500 µl chloroform:methanol 2:1v/v, spun at 13000 rpm for 2 mins and the supernatant retained, dried under $N_2$, resuspended in 10 µl chloroform:methanol:0.22% calcium chloride (60:35:8 v/v/v) and separated by TLC (Silica gel 60 plates, Merck, BDH, Poole, Dorset, UK) in chloroform:methanol: calcium chloride (60:35:0.22%), sprayed with orcinol and visualized by heating to 80° C. for 10 mins.

Figure 1:
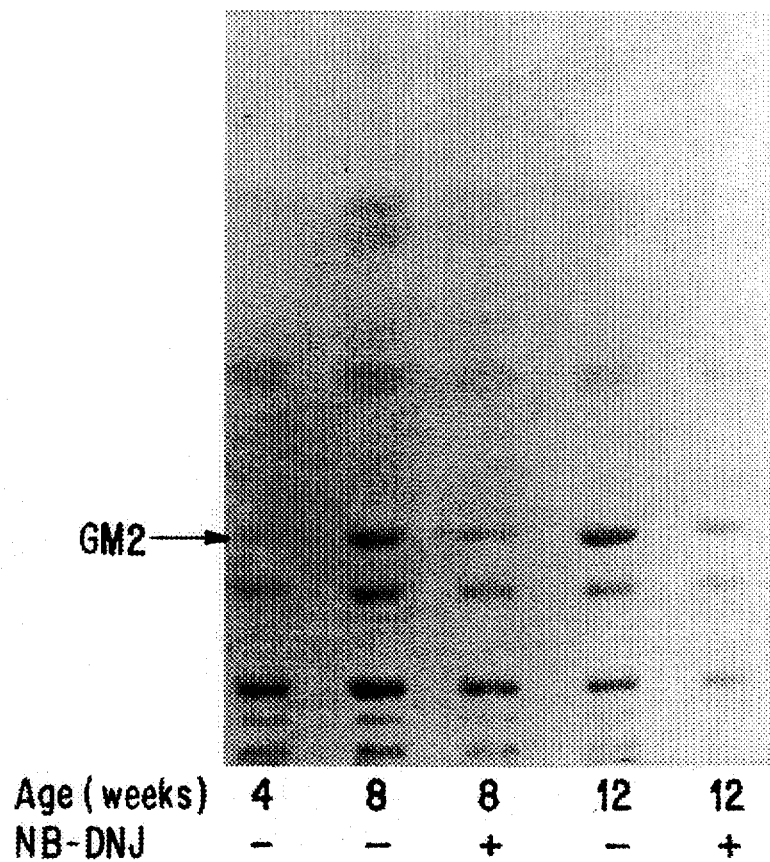
FIG. 1 shows thin layer chromatography (TLC) analysis of GM2 ganglioside storage in the Tay-Sachs mouse in the presence or absence of N-butyl deoxynojirimycin (NB-DNJ). Mice were treated with NB-DNJ from 4 weeks of age up to twelve weeks and their GSL (glycosphingolipid) profiles compared at 4, 8 and 12 weeks relative to the untreated age matched controls. Each lane on the TLC plate represents the base-resistant GSLs derived from the whole brain of an individual mouse. The data are representative of studies carried out on five mice at each time point. The migration position of an authentic GM2 standard is indicated with an arrow.

By four weeks of age a storage band corresponding to GM2 was detectable in the untreated mice, in agreement with previously published reports on this mouse model (9). As expected on the basis of published studies (9), the accumulation of GM2 in the untreated mice progressively increased with increasing age of the mice (FIG. 1).

However, in the NB-DNJ treated mice by eight weeks of age (four weeks untreated from birth to weaning, 4 weeks NB-DNJ treated post-weaning) there was an unexpected reduction in the intensity of the GM2 ganglioside band, relative to the untreated age matched controls, indicating that reduced levels of storage were occurring in the presence of the drug. The mice were followed for twelve weeks and there was a consistent reduction in stored GM2 ganglioside in all animals from the NB-DNJ treated group, irrespective of their age (FIG. 1).

Figure 2A:
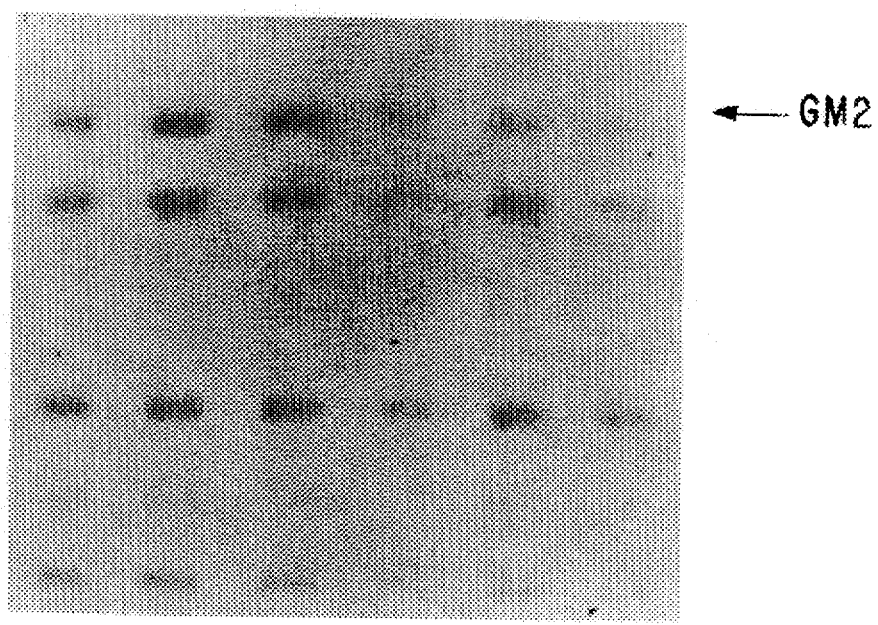
FIG. 2A: TLC profiles on total brain GSLs for three untreated mice (−) and three NB-DNJ treated mice (+).
Figure 2B:
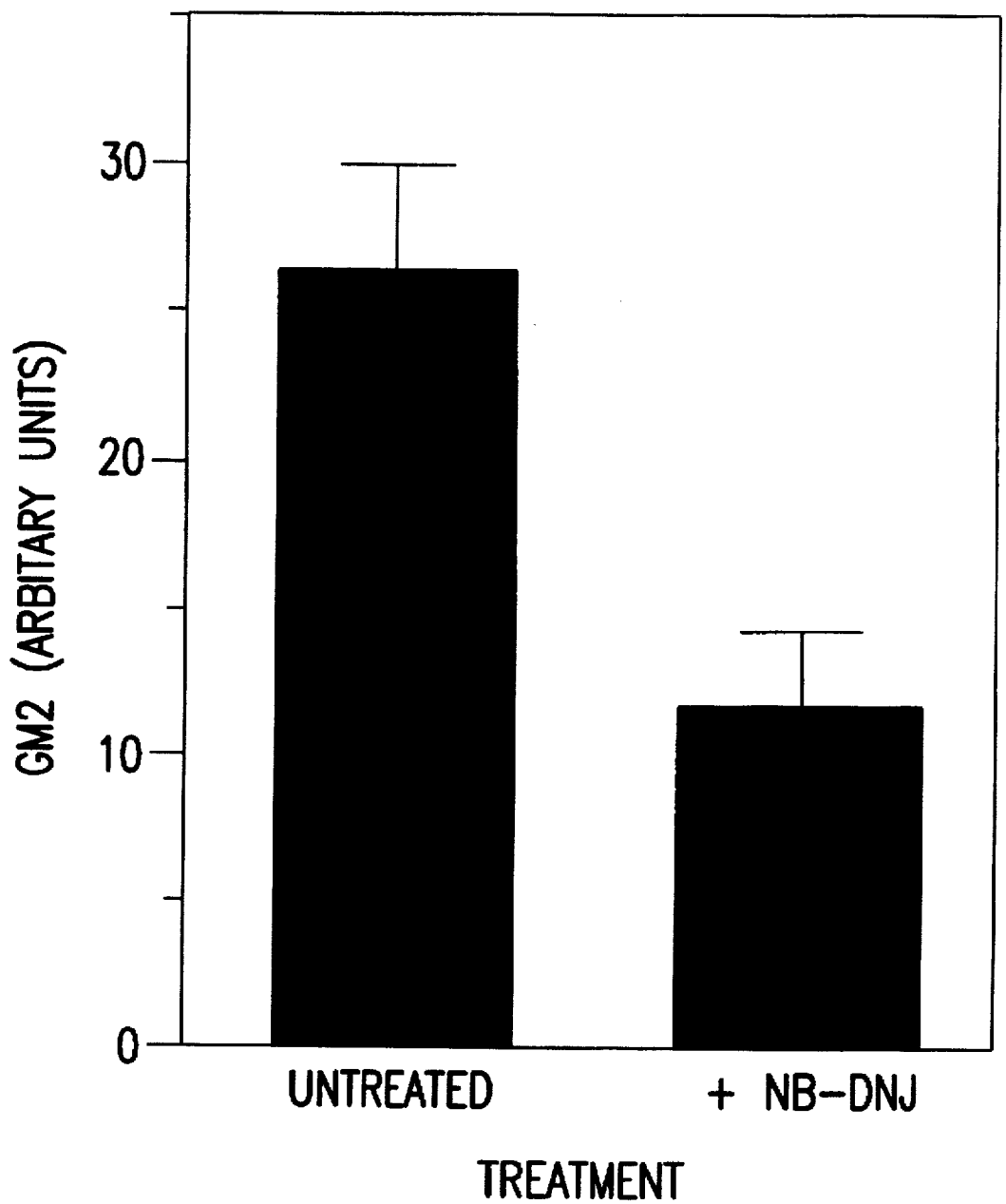
FIG. 2B: Scanning densitometry on the GM2 species from FIG. 2A expressed in arbitrary units. The mean values +/− standard deviation are shown.

To examine the generality of these data a group of three untreated and three NB-DNJ treated mice were evaluated at 12 weeks (FIG. 2A). In all cases, the intensity of the GM2 band was significantly reduced in the NB-DNJ treated animals, relative to the untreated age matched controls. When scanning densitometry was performed on the TLC profiles it was found that there was an approximately 50% reduction in GM2 ganglioside in the treated mouse brains relative to the untreated controls (FIG. 2B).

EXAMPLE III

The neurons within the Tay-Sachs mouse brains which are responsible for the GM2 storage observed in whole brain lipid extracts are confined to certain specific regions of the brain (12). We therefore carried out cytochemical analysis on tissue sections from untreated mice and mice treated for 16 weeks with NB-DNJ using periodic acid-Schiff (PAS) staining to detect the stored ganglioside within the storage neurons (9), as follows:

Mice were anesthetized, perfused with phosphate buffer pH 7.4 containing 4% paraformaldehyde and the brain dissected and retained in fixative overnight prior to cryopreservation and sectioning. Frozen brain sections (7 micron) were warmed to room temperature, stained with periodic acid-Schiff (PAS) according to the manufacturer's instructions (Sigma, Poole Dorset UK), counter-stained with Erhlich's hematoxylin and mounted in DPX (BDH).

It has previously been demonstrated in these untreated mice that the distribution of neurons staining with PAS is coincident with neurons which immunostain with an antibody specific for GM2 ganglioside (9).

Figure 3A:
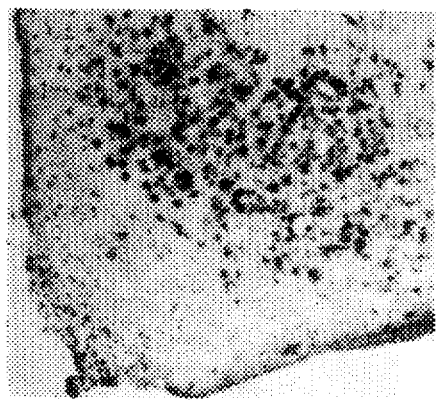
FIG. 3A: Untreated mouse, 10× magnification.
Figure 3B:
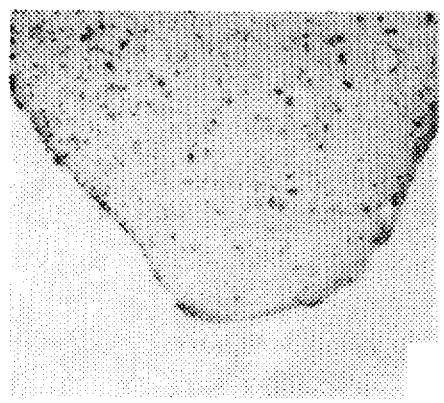
FIG. 3B: NB-DNJ treated mouse, 10× magnification.
Figure 3C:
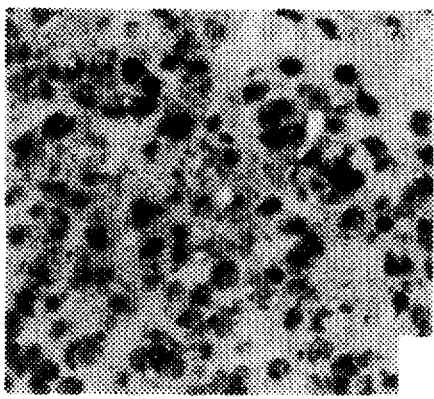
FIG. 3C: Untreated mouse, 25× magnification.
Figure 3D:
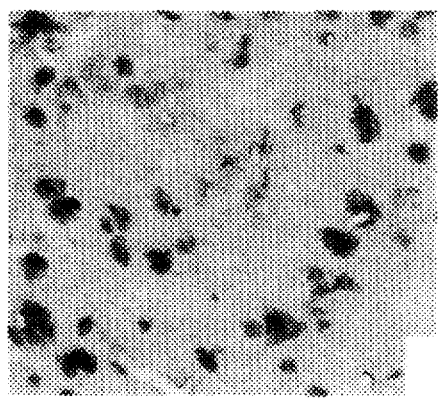
FIG. 3D: NB-DNJ treated mouse, 25× magnification.

In storage regions of the brain, such as the ventromedial hypothalamic nucleus, the NB-DNJ treated mice had fewer PAS positive neurons and the intensity of staining in each neuron was reduced (FIGS. 3B and 3D), relative to the untreated age matched control's brain sections, which exhibited extensive storage (FIGS. 3A and 3C).

The status of the GM2 storage in individual neurons from treated and untreated mouse brains was examined by electron microscopy (EM) as follows:

The mice were anesthetized and perfusion fixed with 2% paraformaldehyde, 2% glutaraldehyde mix in PBS. The brain was dissected and fixed in the same fixative overnight at 4° C. The brain was trimmed and 100 µm sections cut on a vibrotome, the sections washed three times in 0.1 M phosphate buffer and stained with osmium tetroxide (1% in 0.1 M phosphate) for 35 mins. The sections were dehydrated through an ethanol series, treated with propylene oxide (2×15 mins) and placed in Durcupan resin overnight at room temperature, transferred to glass slides and placed at 60° C. for 48 hours.

Storage areas of the brain were selected microscopically, cut out of the thick section with a scalpel blade and glued with Super Glue Loctite, Quick Tite, (Loctite Corp., Rock Hill, Conn.) onto an Embed 800 stub (Electron Microscopy Sciences, Fort Washington, Pa.). Sections were stained with uranyl acetate/lead citrate and observed with a Hitachi 600 microscope at 75 kv.

In the storage neurons from untreated Tay-Sachs mouse brains there were prominent regions of the cytoplasm containing large numbers of membranous cytoplasmic bodies (MCBs) containing the stored lipid product (FIG. 4A). In contrast, in the NB-DNJ treated mice it proved difficult to find storage neurons. However, when storage cells could be located they contained MCBs with greatly reduced electron dense contents (FIG. 4B).

Furthermore, the extensive storage observed within storage neurons from untreated mice resulted in the organelles with the highest degree of storage being difficult to section, with the storage product frequently detaching partially from the surrounding membrane (FIG. 4A). In the NB-DNJ treated mouse brains the storage within neurons was always markedly reduced, relative to the untreated controls, and as a result no sectioning artifact was observed (FIG. 4B). This was consistently observed by two independent electron microscopy groups studying independent material derived from these mice. One representative set of data is shown in FIG. 4.

The EM data are in keeping with the cytochemical staining which indicated that there were fewer storage neurons in the brains of treated mice and that storage cells in the treated animals had reduced levels of GM2 storage, relative to the untreated controls. When the morphology of individual MCBs from untreated and NB-DNJ treated mice were compared under high magnification by EM there was a profound difference in their morphology.

The NB-DNJ treated mice had MCBs which contained less electron dense storage lipid (FIG. 4D) but also did not have the prominent concentrically arranged lamellae characteristic of the MCB in neurons from untreated mice (FIG. 4C). Instead, they exhibited a diffuse pattern of storage with membrane-like structures only clearly discernible in the periphery of the organelle (FIG. 4D). Taken together with the cytochemical data, this demonstrates that NB-DNJ prevents lysosomal storage and the extent of storage per cell and per MCB is dramatically reduced, in keeping with the biochemical data on whole brain GSLs (FIGS. 1 and 2).

The data outlined herein demonstrate that oral treatment of mice with NB-DNJ is well tolerated and that it results in the inhibition-of GSL biosynthesis. Furthermore, in the Tay-Sachs mouse, which exhibits progressive CNS storage of GM2 ganglioside, we have been able to prevent storage, as a consequence of reducing GSL biosynthesis. This indicates that NB-DNJ can cross the blood:brain barrier to an extent which can prevent storage.

This therefore indicates that substrate deprivation resulting from NB-DNJ administration is a rational strategy for the therapy of the human GSL lysosomal storage diseases. It has been shown in vitro that NB-DNJ specifically inhibits the first step in GSL biosynthesis, the glucosyl-transferase catalyzed biosynthesis of GlcCer (5-7).

As several of the human glycosphingolipid (GSL) storage diseases involve the storage of GlcCer-based GSLs, this therapeutic strategy can be applied to all of these disease states, irrespective of the specific storage product. This would include Gaucher (types 1, 2 and 3), Fabry disease, Tay-Sachs disease, Sandhoff disease, GM1 gangliosidosis, and fucosidosis.

The current application of enzyme replacement to Gaucher disease is limited by the fact that the enzyme cannot cross the blood:brain barrier and hence this therapy is only efficacious in type 1 disease where there is no neuropathology involved. Our finding that GSL depletion can be achieved in the central nervous system is therefore of major significance as it means that all the GSL storage diseases could be treated with NB-DNJ, as many of them involve neuropathology in the CNS.

NB-DNJ does not appear to inhibit galactosyltransferase which initiates the biosynthesis of the pathway that results in the formation of GalCer and sulphatide. Therefore, it is not believed that NB-DNJ would show efficacy against Krabbe disease and metachromatic leukodystrophy (MLD). These diseases involve the storage of GalCer and sulphatide, respectively, as shown at the bottom of FIG. 5. This can be advantageous to the invention as the formation of GalCer and sulphatide, which are important constituents of myelin, would not be affected by the treatment. Hence, myelination and myelin stability would not be impaired.

EXAMPLE IV

When any of the following compounds are substituted for an equivalent amount of 1,5-(Butylimino)-1,5-dideoxy-D-glucitol in the above Examples I, II and III, substantially similar inhibitory results are obtained:

A) 1,5-(Hexylimino)-1,5-dideoxy-D-glucitol;
B) 1,5-(Butylimino)-1,5-dideoxy-D-galactitol;
C) 1,5-(Hexylimino)-1,5-dideoxy-D-galactitol;
D) 1,5-(Butylimino)-1,5-dideoxy-D-glucitol, tetrabutyrate;
E) 1,5-(Hexylimino)-1,5-dideoxy-D-glucitol, tetraacetate.

Compounds D and E are synthesized as described in U.S. Pat. No. 5,003,072.

In treatment of the recipient patients in accordance with the method of the invention, the active agent can be administered by conventional drug administration procedures, preferably in formulations with pharmaceutically acceptable diluents and carriers. The active agent can be used in the free amine form or in the salt form. Pharmaceutically acceptable salt forms are illustrated, for example, by the HCl salt.

The amount of active agent to be administered must be an effective amount, that is, an amount which will be medically beneficial but does not present toxic effects which overweight the advantages which accompany its use. It would be expected that the average adult human daily dosage would normally range from about 0.1 mg to about 1000 mg of the active agent.

The preferable route of administration is orally in the form of capsules, tablets, syrups, elixirs and the like, although parenteral administration can also be had. Suitable formulations of the active compound in pharmaceutically acceptable diluents and carriers in therapeutic dosage form can be prepared by conventional procedures such as by reference to general texts in the field, e.g., Remington's Pharmaceutical Sciences, ed. Arthur Osol, 16th ed., 1980, Mack Publishing Co., Easton, Pa., and the 18th ed., 1990. Conventional diluents and carriers are, e.g., water, normal saline, sugars, starch and the like substances.

Various other examples will be apparent to the person skilled in the art after reading the disclosure herein. All such other examples are meant to be included within the scope of the appended claims.

REFERENCES

1. Neufeld, E. F. (1991) Ann. Rev. Biochem., 60, 257–280.
2. Beutler, E. (1992) Science, 256, 794–799.
3. Barton, N. W., Brady, R. O., Dambrosia, J. M., Di Bisceglie, A. M., Doppelt, S. H., Hill, S. C., Mankin, H. J., Murray, G. J., Parker, R. I., Argoff, C. E., Grewal, R. P., Yu, K-T., and Collaborators (1991) N. Eng. J. Med. 324, 1464–1470.
4. Beutler, E., Kay, A., Saven, A., Garver, P., Thurston, D., Dawson, A. and Rosenbloom, B. (1991) Blood, 78, 1183–1189.
5. Platt, F. M., Neises, G. R., Dwek, R. A. and Butters, T. D. (1994) J. Biol Chem., 269, 8362–8365.
6. Platt, F. M., Neises, G. R., Dwek, R. A. and Butters, T. D. (1994) J. Biol Chem., 269, 27108–27114.
7. Platt, F. M. and Butters, T. D. (1995) Inhibitors of Glycosphingolipid Biosynthesis. Trends in Glycoscience and Glycotechnology. 269, 495–511.
8. Yamanaka, S., Johnson, M. D., Grinberg, A., Westphal, H., Crawley, J. N., Taniike, M., Suzuki, K. and Proia, R. L. (1994) Proc. Natl. Acad. Sci. U.S.A., 91, 9975–9979.
9. Sandhoff, K., Conzelmann, E., Neufeld, E. F., Kaback, M. M., and Suzuki, K. (1989) in The Metabolic Basis of Inherited Disease, eds. Scriver, C. R., Beaudet, A. L., Sly, W. S. and Valle, D. (McGraw-Hill, New York, Vol. 2, pp1807–1839.
10. Sango, K., Yamanaka, S. Hoffmann, A., Okuda, Y., Grinberg, A., Westphal, H., McDonald, M. P., Crawley, J. N., Sandhoff, K., Suzuki, K. and Proia, R. L. (1995) Nature Genet. 11, 170–176.
11. Taniike, M., Yamanaka, S., Proia, R. L., Langaman, C., Bone-Turrentine, T. and Suzuki, K. (1995) Acta Neuropathol. 89, 296–304.
12. Fischl, M. A., Resnick, L., Coombs, R., Kremer, A. B., Pottage, J. C., Fass, R. J., Fife, K. H., Powderly, W. G., Collier, A. C., Aspinall, R. L., Smith, S. L., Kowalski, K. G., and Wallemark, C-B. (1994) J. AIDS 7, 139–147.

What is claimed:

1. A method for the treatment of a lysosomal storage disease having a significant central nervous system (CNS) involvement in a patient in need thereof comprising administering to said patient a storage-inhibitory effective amount of an N-alkyl derivative of a 1,5-iminosugar in which said alkyl group contains from about 2 to about 8 carbon atoms and said 1,5-iminosugar is 1,5dideoxy-1,5-imino-D-glucitol or 1,5-dideoxy-1,5-imino-D-galactitol, wherein from 1 to 4 of the free hydroxyl groups of said 1,5-iminosugar are optionally O-acylated.

2. The method of claim 1 in which the 1,5-iminosugar is 1,5dideoxy-1,5-imino-D-glucitol.

3. The method of claim 1 in which the alkyl group is butyl.

4. The method of claim 1 in which the 1,5-iminosugar is 1,5dideoxy-1,5-imino-D-glucitol and the alkyl group is butyl.

5. The method of claim 4 in which the 1,5-iminosugar is O-acylated to form the tetrabutyrate.

6. The method of any of claims 1–5 in which the lysosomal storage disease is Tay-Sachs disease.

* * * * *